United States Patent [19]

Hansen et al.

[11] Patent Number: 5,036,062
[45] Date of Patent: Jul. 30, 1991

[54] NOVEL ESTERS

[75] Inventors: Bertil V. Hansen; Per-Olov G. Gunnarsson; Henri R. Mollberg, all of Helsingborg; Sven-Åke Johansson, Ödåkra, all of Sweden

[73] Assignee: Pharmacia AB, Uppsala, Sweden

[21] Appl. No.: 365,436

[22] Filed: Jun. 13, 1989

[30] Foreign Application Priority Data

Jun. 28, 1988 [SE] Sweden ............................... 8802402

[51] Int. Cl.$^5$ ...................... A61K 31/565; C07J 1/00
[52] U.S. Cl. .................................. 514/176; 552/626; 540/109; 514/182
[58] Field of Search ................. 540/109; 552/626; 514/182, 176

[56] References Cited

U.S. PATENT DOCUMENTS

| | | | |
|---|---|---|---|
| 3,299,104 | 1/1967 | Fex | 424/243 |
| 4,443,440 | 4/1984 | Anderson | 424/243 |
| 4,584,136 | 4/1986 | Yoshida et al. | 260/397.5 |
| 4,615,835 | 10/1986 | Eisenbrand et al. | 260/375.5 |

FOREIGN PATENT DOCUMENTS 0104746 8/1983 European Pat. Off. .
962797 11/1960 United Kingdom .

OTHER PUBLICATIONS

Niculescu-Duvaz et al., "New N-yperites of the . . . ", CA 68:29354h (1968).
Burger, A., "A Guide to Drug Design", John Wiley & Sons, p. 15, 1984.

*Primary Examiner*—C. Warren Ivy
*Assistant Examiner*—Celia Chang
*Attorney, Agent, or Firm*—Fred Philpitt

[57] ABSTRACT

The present invention concerns novel compounds having the general formula

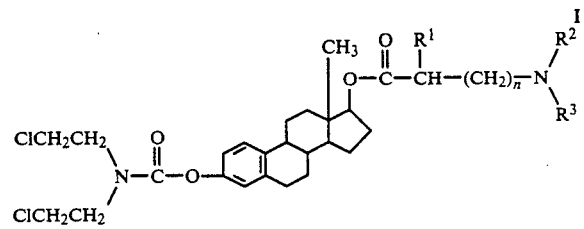

wherein $R^1$, $R^2$ and $R^3$ are selected form the group consisting of hydrogen or lower alkyl having 1-4 carbon atoms, wherein $R^2$ and $R^3$ together with the N atom can also form a ring having 2-5 carbon atoms and wherein n is 0, 1 or 2, and pharmaceutically acceptable salts thereof.

The compounds according to the invention are useful as anticancer agents.

20 Claims, No Drawings

NOVEL ESTERS

The present invention concerns novel esters having anticancer activity. Specifically the invention concerns novel esters of estramustine.

Estramustine, estra-1,3,5(10)-triene-3,17 β-diol 3-/N,N-bis-(2-chloroethyl)carbamate/, and various esters thereof are previously known as antineoplastic agents from e.g. the U.S. Pat. No. 3,299,104. One of these esters, 17-estramustine dihydrogen phosphate ester, or abbreviated EMP, has been further developed and water soluble salts thereof, Estracyt$^R$, are now widely used for treating prostatic cancer. A problem with the water soluble salts of EMP when taken orally concerns the interaction with calcium ions in food and drinks. In the presence of calcium ions these EMP salts give precipitates and form an insoluble complex, which is not absorbed from the gastro-intestinal tract and therefore has very little activity in the body. Several attempts to overcome this problem have been made, both as regards the pharmaceutical preparation of EMP salts and of estramustine as such. It has, however, not been possible to find EMP modifications for oral use, which in the presence of calcium ions produce the same plasma levels of the main EMP metabolites estramustine and the corresponding 17-keto compound, estromustine, as does the water soluble disodium salt of EMP when taken in absence of calcium.

Unexpectedly it has now been found that the problem with the calcium interaction can be avoided and that the plasma levels of estramustine and estromustine as well as the anticancer activity can be maintained at an essentially unchanged or even higher level if the estramustine is administered in the form of certain amino acid esters.

Amino acid esters for pharmaceutical purposes have been described in the British Patent No. 962,797 and in the European Patent Application No. 0104746. The aims of the inventions of these applications, however, are different from the aim of the present invention and the alcohols esterified, although containing a steroid skeleton, have structures widely different from that of estramustine.

The present invention concerns novel compounds having the general formula:

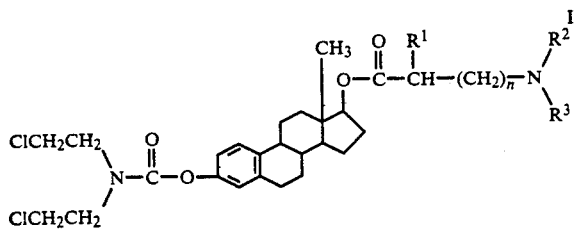

wherein $R^1$, $R^2$ and $R^3$ are selected from hydrogen and lower alkyl having 1-4 carbon atoms, wherein $R^2$ and $R^3$ together with the N atom can form a ring having 2-5 carbon atoms, and wherein n is 0, 1 or 2, and pharmaceutically acceptable salts thereof. Preferred compounds are those where n=0, $R^1$ is hydrogen and $R^2$ and $R^3$ are equal or different and are hydrogen, methyl or ethyl.

The following compounds are especially preferred.
17-estramustine N,N-diethylaminoacetate
17-estramustine 4-(N,N-dimethylamino)butyrate
17-estramustine N-methylaminoacetate
17-estramustine aminoacetate
17-estramustine 2-aminopropionate
17-estramustine N-ethylaminoacetate
17-estramustine N-(2-propyl)aminoacetate
17-estramustine 3-aminopropionate
17-estramustine N-(1-propyl)aminoacetate The novel compounds are normally prepared from estramustine using conventional methods, two of them being mentioned below. The preparation of estramustine itself is disclosed in e.g. the U.S. Pat. No. 3,299,104.

In one of the methods estramustine is esterified with an acid containing a reactive substituent such as halogen, e.g. chloro, bromo, iodo, or organic sulfonyloxy, organic being a hydrocarbon residue, containing 1 to 6 carbon atoms, giving an intermediate having formula II,

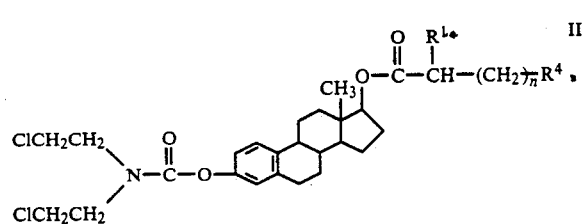

where $R^4$ is the reactive substituent. The intermediate is then reacted with amines $HNR^2R^3$ giving the novel compounds having formula I.

According to the other method estramustine is esterified with an amino acid having the general formula

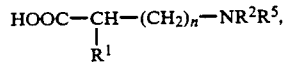

wherein $R^5$ is $R^3$ or optionally a protecting group, giving an intermediate having the general formula II, wherein $R^4$ is $-NR^2R^5$, from which the protecting group is afterwards removed for the preparation of compounds having the general formula I. Examples of substituents $R^5$ protecting the amino group are t-butoxycarbonyl and benzyloxycarbonyl.

For the esterification well known methods are used. One type of method is based on reactions with reactive derivatives of the acids such as acyl chlorides, bromides and mixed anhydrides with organic acids including those obtained from lower alkyl chloroformates. Another type of method is based on reactions with acids in the presence of dehydrating agents, e.g. 1,1-carbonyldiimidazole and N,N'-dicyclohexylcarbodiimide.

The salts of the novel compounds are prepared from the baseform of the compound and pharmaceutically accepted acids, e.g. those listed in International Journal of Pharmaceutics 3, 202 (1986), which is hereby incorporated by reference. Preferred acids are hydrochloric acid, hydrobromic acid, methanesulfonic acid and ethanesulfonic acid.

Among the salts of the novel compounds the following are specially preferred: 17-estramustine N-methylaminoacetate, hydrochloride; 17-estramustine aminoacetate, hydrochloride; 17-estramustine N-methylaminoacetate, methanesulfonate; 17-estramustine aminoacetate, methanesulfonate; 17-estramustine N-methylaminoacetate, ethanesulfonate and 17-estramustine aminoacetate, ethanesulfonate.

Although the compounds according to the invention are at first hand intended for oral use it is obvious that other ways of administration are within the scope of the invention.

Pharmaceutical formulations are thus usually prepared from a predetermined quantity of one or more of the compounds of the invention. Such formulations may take the form of powders, granules (pellets), suppositories, capsules or tablets, suspensions, etc. with or without, but preferably with, any one of a large variety of pharmaceutically acceptable excipients. When in a mixture with a pharmaceutical vehicle or carrier, the active ingredient usually comprises from about 0.01 to 95 percent, normally from about 0.05 to about 80 percent, by weight of the composition. Carriers such as cellulose, sugar, talc, commonly used synthetic and natural gums, natural and synthetic oils, emulsifying and dispersing agents, water, and the like, may be used in such formulations. Binders such as polyvinylpyrrolidone and lubricants such as magnesium stearate, may be used to form tablets. Disintegrating agents such as starch may also be included in tablets.

The compositions are preferably formulated in a unit dosage form, each dosage containing from about 0.05 to about 1000 mg, more usually about 5 to about 300 mg of the active ingredient. The term "unit dosage form" refers to physically discrete units suitable as unitary dosages for human subjects and other mammals, each unit containing a predetermined quantity of the new ester calculated to produce the desired therapeutic effect, in association with the required pharmaceutical carrier.

The compound according to the invention is effective over a wide dosage range. For example, dosages per day will normally fall within the range of about 0.1 to about 100 mg/kg of body weight. In the treatment of adult humans, the range of about 0.5 to about 50 mg/kg, in single or divided doses, is preferred. It will be understood that the amount of the compound actually administered will be determined by a physician, in the light of the relevant circumstances including the condition to be treated, the chosen route of aministration, the age, weight, and response of the individual patient, and the severity of the patient's symptoms, and therefore the above dosage ranges are not intended to limit the scope of the invention in any way. As used herein the terms "pharmaceutical compositions" and "pharmaceutically acceptable" include compositions and ingredients for both human and veterinary use.

The following examples are intended to illustrate but not to limit the scope of the invention, although the compounds named are of particular interest for our intended purposes.

EXAMPLE 1

17-Estramustine chloroacetate

Estramustine (4.4 g, 0,01 mol) is dissolved in toluene (100 ml). Chloroacetyl chloride (1.7 g, 0.015 mol) is added and the solution is heated at 70° C. for 1.5 hours. The solvent is then removed in a rotary evaporator at 30° C. The residue is treated with ethanol (40 ml) and the product crystallizes. The product is collected on a filter and washed with a few ml of ethanol. The chloroacetate after drying at room temperature melts at 95° C. Yield 4.9 g.

EXAMPLE 2

17-Estramustine bromoacetate

This compound is prepared by a method similar to the one described in example 1 from estramustine and bromoacetyl bromide. M.p. 109° C.

EXAMPLE 3

17-Estramustine N-methylaminoacetate, hydrochloride

17-Estramustine chloroacetate (5.2 g, 0.01 mol) is dissolved in acetonitrile (40 ml) at room temperature. Methylamine (3.1 g) (0.1 mol) dissolved in cold acetonitrile (10 ml) at 0° C. is added. After 3 h the excess of amine and the solvent is removed in a rotary evaporator. The residue is dissolved in methylene chloride (50 ml) and washed three times with 50 ml water, pH being adjusted each time to 7-9 with a sodium bicarbonate solution. The methylene chloride solution is dried over anhydrous sodium sulfate and the solvent is carefully evaporated. The residue is dissolved in acetonitrile (40 ml) and the N-methylaminoacetate ester is precipitated by the addition of a solution of hydrogen chloride in ether (0.012 mol). A voluminous precipitate is formed which after stirring for a few minutes disintegrates to fine crystals. The product is collected on a filter and washed with a mixture of ethylacetate and acetonitrile (1:1). The hydrochloride is then dried under vacuum at room temperature for 24 h. Yield 3.7 g. M.p. 226° C., with decomposition. NMR spectroscopy shows that the structure of the product is estramustine 17-N-methylaminoacetate.

EXAMPLE 4

17-Estramustine N-methylaminoacetate, methanesulfonate and ethanesulfonate

Using the method described in example 3 except for using a solution of methanesulfonic acid or ethanesulfonic acid in ether instead of hydrogen chloride in ether a methanesulfonate, m.p. 212° C., or an ethanesulfonate, m.p. 170° C., respectively, are obtained (compounds Nos. 4:1 and 4:2, respectively).

EXAMPLE 5

17-Estramustine N-$R^2$-N-$R^3$-aminoacetate, hydrochloride

Esters having the amino substituents $R^2$ and $R^3$ described in table 1 are made from 17-estramustine bromoacetate using the method of example 3 with minor modifications.

TABLE 1

| $R^2$ | $R^3$ | Hydrochloride m.p. °C. | Amine used |
|---|---|---|---|
| —$CH_3$ | —$CH_3$ | 210 | $(CH_3)_2NH$ |
| H | —$CH_2CH_3$ | 220 | $CH_3CH_2NH_2$ |
| H | —$CH_2CH_2CH_3$ | 170 | $CH_3CH_2CH_2NH_2$ |
| H | —$CH(CH_3)_2$ | 200 | $(CH_3)_2CHNH_2$ |
| H | —$C(CH_3)_3$ | 172 | $(CH_3)_3CNH_2$ |
| —$CH_2CH_3$ | —$CH_2CH_3$ | 158 | $(CH_3CH_2)_2NH$ |
| —$CH_2$—$CH_2$—$CH_2$—$CH_2$— | | 210 | 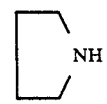 |

EXAMPLE 6

17-Estramustine aminoacetate, hydrochloride and methanesulfonate

Estramustine (4.4 g, 0.01 mol) and N-tert-butoxycarbonylglycine (1.75 g, 0.01 mol) are dissolved in methylene chloride (35 ml). Dicyclohexylcarbodiimide (2.1 g, 0.01 mol) and 4-dimethylaminopyridine (0.1 g, 0,001 mol) are added and the reaction mixture is stirred for 3 hours. The dicyclohexylurea formed is removed by filtration and the solvent is carefully evaporated. The oily residue is dissolved in acetonitrile (10 ml). Acetonitrile (40 ml) containing hydrogen chloride (0.03 mol) is added and the mixture is stirred for 16 hours. The precipitate formed is collected on a filter and recrystallized from methanol/ether. Yield 3.2 g of 17-estramustine aminoacetate, hydrochloride, (m.p. 220° C., compound No. 6:1) as confirmed by NMR-spectro-scopy.

With the same method except for using methanesulfonic acid (0.03 mol) instead of hydrogen chloride and omitting the recrystallization 17-estramustine aminoacetate, methanesulfonate (compound No. 6:2) is obtained, m.p. 206° C.

EXAMPLE 7

17-Estramustine aminopropionates, hydrochlorides

Using the method described in example 6 the following salts are obtained:
17-estramustine 2-L-aminopropionate, hydrochloride, m.p. 248° C., from N-tert-butoxycarbonyl-L-alanine
17-estramustine 3-aminopropionate, hydrochloride, m.p. 223° C., from N-tert-butoxycarbonyl-$\beta$-alanine

EXAMPLE 8

17-Estramustine aminoacetate, methanesulfonate

To estramustine (4.4 g, 0.01 mol) dissolved in methylene chloride (30 ml) is added N-benzyloxycarbonylglycine (2.2 g, 0.01 mol), dicyclohexylcarbodiimide (2.25 g, 0,011 mol) and 4-dimethylamino-pyridine (0.12 g, 0.001 mol). The mixture is stirred at room temperature for 2 h. The dicyclohexylurea formed is removed by filtration. The filtrate is washed with hydrochloric acid (2 mol/l, 10 ml), water (10 ml), sodium carbonate solution (1 mol/l, 25 ml) and with water (25 ml) and dried with sodium sulfate. The solvent is evaporated in a rotary evaporator. The residual oil is dissolved in ethanol (125 ml). Palladium on carbon (1 g, Pd-content 5%) is added and the mixture is treated with hydrogen at atmospheric pressure and room temperature. When the reaction has ceased the mixture is filtered and the solvent is evaporated carefully. The residue is dissolved in acetonitrile (75 ml). Methanesulfonic acid (1 g, 0.01 mol) is added. After stirring of the mixture for 18 h the precipitate is collected on a filter and washed with acetonitrile and dried at room temperature. Yield 3.7 g of 17-estramustine aminoacetate, methanesulfonate, m.p. 204° C.

EXAMPLE 9

17-Estramustine 4-(N,N-dimethylamino)butyrate, hydrochloride

To estramustine (4.4 g, 0,01 mol) in methylene chloride (50 ml) is added 4-dimethylaminobutyryl chloride, hydrochloride, (1,3 g, 0.01 mol). The solution is refluxed for 2 h. The solvent is evaporated and the resulting oil crystallizes. The product is treated with activated carbon in ethanol solution and recrystallized from ethanol/ether. Yield 6.5 g. M.p. 205° C. The product is 17-estramustine 4-(N,N-di-methylamino)butyrate, hydrochloride, as confirmed by NMR-spectroscopy.

EXAMPLE 10

Interactions with calcium ions

Solution A: 0.3 mole/l calcium diethanesulfonate. Calcium carbonate (1.38 g, 15 mmole) is dissolved by adding a 1.0 mole/l ethanesulfonic acid solution until a stable pH=5.3 is obtained. The solution is diluted with water to 50 ml.

Solution B: 0.03 mole/l calcium diethanesulfonate. One part of solution A is diluted with 9 parts of water.

Solution C: 0.05 mole/l sodium acetate/acetic acid buffer with pH=4.5. Glacial acetic acid (3.0 g, 0.05 mole) is dissolved in 800 ml of water, titrated with 1 mole/l sodium hydroxide solution to pH=4.5 and diluted to 1 l.

The test compound is dissolved in 50 ml of solution C. A clear solution is obtained in a few minutes. After 5 minutes an equimolar amount of calcium ions are added by adding 1 ml of solution A or B. The mixture is observed for 3 h.

| Test Compound | Amount mg | mmole | Solution added, mmole calcium ions | Observation |
|---|---|---|---|---|
| Estramustine phosphate, disodium salt | 16 | 0.03 | B, 0.03 | Becomes unclear immediately |
| Compound No. 6:2 | 178 | 0.3 | A, 0.3 | Remains clear |
| Compound No. 4:2 | 186 | 0.3 | A, 0.3 | " |

The results show that the novel compounds in the presence of calcium ions do not give any precipitate at concentrations 10 times higher than the concentrations of estramustine phosphate disodium salt and calcium ions required to give an immediate formation of an undissolved estramustine phosphate calcium salt.

EXAMPLE 11

Comparison of estramustine phosphate and novel estramustine esters with respect to oral bioavailability of estramustine in dogs Different formulations were administered orally to groups of four Beagle dogs. The dose was equivalent to 140 mg of estramustine phosphate. The animals were fasting before dosing and given 50 ml 0.01 M hydrochloric acid after the dose. Blood samples were analysed for estramustine by means of gas chromatography. (Andersson, S-B, et al., Acta Pharm.Suec. 19, 1 (1982).

The following formulations were used:
1. Water solution of estramustine phosphate disodium salt
2. Water solution of compound No. 6:2
3. Water solution of compound No. 4:2

Table 1 shows the areas under the plasma concentration versus time curves, AUC, of estramustine in dogs. The mean values were 54+62, 118+60 and 83+62 ng/mlxhours for estramustine phosphate, compound No. 6:2 and No. 4:2, respectively.

TABLE 1

Oral bioavailability of estramustine in dogs. AUC-values after administration of solutions of the estramustine esters

| Dog No. | Etramustine phosphate disodium salt | Compound No. 6:2 | Compound No. 4:2 |
|---|---|---|---|
| 8727 | 147 | 100 | — |
| 8729 | 16.4 | 140 | 94.0 |
| 8731 | 34.0 | 45.8 | 79.8 |
| 8733 | 19.5 | 184.8 | — |
| 8735 | — | — | 2.6 |
| 8742 | — | — | 153.4 |
| Mean ± S.D. | 54.3 ± 62.4 | 118 ± 59 | 82.6 ± 62.0 |

EXAMPLE 12

Formulation, Plain Tablets

| I | Compound No. 6:2, mg | 160 |
|---|---|---|
|   | Corn starch, mg | 15 |
| II | Polyvidone, mg | 8 |
|   | Ethanol | q.s. |
| III | Corn starch, mg | 15 |
|   | Magnesium stearate, mg | 2 |

I is mixed and granulated with solution II. After drying and milling through 1 mm sieve III is added. The mixture is compressed to tablets with a weight of 200 mg.

EXAMPLE 13

Formulation, Capsules

The mixture from example 12 is filled into hard capsules, size No. 1.

We claim:

1. Novel compounds having the general formula

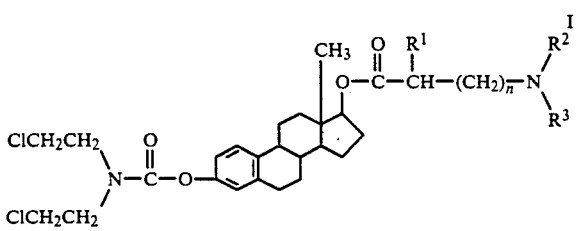

wherein $R^1$, $R^2$ and $R^3$ are selected from the group consisting of hydrogen or lower alkyl having 1–4 carbon atoms, wherein $R^2$ and $R^3$ together with the N atom can also form a ring having 3–6 members and wherein n is 0, 1 or 2, and pharmaceutically acceptable salts thereof.

2. Compounds according to claim 1 wherein n is 0.

3. Compounds according to claim 1 wherein $R^1$ is hydrogen.

4. Compounds according to claim 1, wherein $R^2$ and $R^3$ are equal or different and consist of hydrogen, methyl or ethyl.

5. A compound according to claim 1 selected from the following group:
17-estramustine N,N-diethylaminoacetate
17-estramustine 4-(N,N-dimethylamino)butyrate
17-estramustine N-methylaminoacetate
17-estramustine aminoacetate
17-estramustine 2-aminopropionate
17-estramustine N-ethylaminoacetate
17-estramustine N-(2-propyl)aminoacetate
17-estramustine 3-aminopropionate
17-estramustine N-(1-propyl)aminoacetate 6. A compound according to claim 1 selected from the following group:
17-estramustine N-methylaminoacetate, hydrochloride
17-estramustine aminoacetate, hydrochloride
17-estramustine N-methylaminoacetate, methanesulfonate
17-estramustine aminoacetate, methanesulfonate
17-estramustine N-methylaminoacetate, ethanesulfonate
17-estramustine aminoacetate, ethanesulfonate 7. Compounds according to claim 2 wherein $R^1$ is hydrogen.

8. Compounds according to claim 2 wherein $R^2$ and $R^3$ are equal or different and consist of hydrogen, methyl or ethyl.

9. Compounds according to claim 7 wherein $R^2$ and $R^3$ are equal or different and consist of hydrogen, methyl or ethyl.

10. Compounds according to claim 8 wherein $R^2$ and $R^3$ are equal or different and consist of hydrogen, methyl or ethyl.

11. A compound according to claim 1 which is 17-estramustine-2-L-amino-propionate, hydrochloride.

12. A compound according to claim 1 which is 17-estramustine N,N-diethylaminoacetate.

13. A compound according to claim 1 which is 17-estramustine 4-(N,N-dimethylamino)butyrate.

14. A compound according to claim 1 which is 17-estramustine N-methylaminoacetate.

15. A compound according to claim 1 which is 17-estramustine aminoacetate.

16. A compound according to claim 1 which is 17-estramustine 2-aminopropionate.

17. A compound according to claim 1 which is 17-estramustine N-ethylaminoacetate.

18. A compound according to claim 1 which is 17-estramustine N-(2-propyl)aminoacetate.

19. A compound according to claim 1 which is 17-estramustine 3-aminopropionate.

20. A pharmaceutical composition containing as an active ingredient a compound as set forth in claim 1 and a pharmaceutically acceptable carrier.

* * * * *